United States Patent [19]
Ishikawa et al.

[11] Patent Number: 4,755,041
[45] Date of Patent: Jul. 5, 1988

[54] EYE REFRACTIVE POWER MEASURING APPARATUS

[75] Inventors: Yasuyuki Ishikawa, Yokohama; Takashi Masuda, Kawasaki; Toshio Sakane, Sagamihara, all of Japan

[73] Assignee: Canon Kabushiki Kaisha, Tokyo, Japan

[21] Appl. No.: 682,319

[22] Filed: Dec. 17, 1984

[30] Foreign Application Priority Data

Dec. 30, 1983 [JP] Japan .................... 58-246577

[51] Int. Cl.$^4$ .............................................. A61B 3/10
[52] U.S. Cl. .................................................... 351/211
[58] Field of Search ................................ 351/206, 211

[56] References Cited

U.S. PATENT DOCUMENTS 4,376,573  3/1983  Matsumura ..................... 351/211
4,408,847  10/1983  Wada ............................ 351/211
4,421,391  12/1983  Matsumura ..................... 351/211
4,431,278  2/1984  Nohda .

Primary Examiner—Rodney B. Bovernick
Attorney, Agent, or Firm—Fitzpatrick, Cella, Harper & Scinto

[57] ABSTRACT

An eye refractive power measuring apparatus having a unit for projecting a plurality of index images onto the fundus of an eye to be examined, a unit for detecting the eye fundus reflected light beams of the index images correspondingly to each measuring meridian direction, a unit for operating the refractive power of the eye on the basis of the output of the detecting means, a unit for moving a fixation target for fixing the eye to be examined thereto or the projection system thereof in the direction of the optic axis, and a unit for controlling the movement speed of the fixation target or the projection system thereof on the basis of the degree of variation in the result of the measurement of the operated refractive power of the eye which results from the movement.

4 Claims, 2 Drawing Sheets

EYE REFRACTIVE POWER MEASURING APPARATUS

BACKGROUND OF THE INVENTION

1. Field of the Invention

This invention relates to an eye refractive power measuring apparatus for alleviating the adjusting power of an eye to be examined and measuring the refractive power of the eye.

2. Description of the Prior Art

Generally, when the refractive power of an eye is to be measured, it is a rule to effect the measurement in a state in which the adjusting power of the eye to be examined is loosened. However, where a target image to which the examinee's line of sight is to be fixed is optically formed in a light-intercepting housing and the examinee is caused to see this target image as has heretofore been practiced, the state of so-called mechanical near-sightedness is often brought about by the adjusting power being caused to come into play by looking into the target image.

In order to avoid such a state, various means to which the means called the cloud-mist type is applied have heretofore been developed and incorporated into an eye refractive power measuring apparatus. However, in the apparatus of this type, convex lenses must be loaded by an appropriate amount corresponding to the refractive power of the eye to be examined and if too many convex lenses are used, there may be brought about a reverse effect. Moreover, it is difficult to apply appropriate cloud-mist to the refractive power of the eye to be examined which is not yet known, and in addition, the eye to be examined widely ranges from intense short-sightedness exceeding −10 diopters to a lens-free eye exceeding +10 diopters. The amount of mechanical short-sightedness occurring when the eye to be examined looks into the target image may vary greatly with age or different individuals and it is more difficult to apply appropriate cloud-mist to the refractive power of such eye. Accordingly, to apply appropriate cloud-mist, it becomes necessary to correct the position of the target image with the value of refraction measured under predetermined conditions as a reference.

However, the problem is the relation between the speed at which the position of the target image is corrected and the responsiveness of the eye to be examined. That is, if the position of the target image is changed fast, the examinee cannot know what has happened, and the state of adjustment of the eye will not vary or a contrary result will be brought about. Conversery, if the target image is moved slowly, too much time will be required and this will impart an extra burden to the examinee and, in the meantime, his line of sight will fluctuate and make accurate measurement impossible.

SUMMARY OF THE INVENTION

It is an object of the present invention to provide an eye refractive power measuring apparatus in which a fixation target is controlled so as to loosen the adjustment of an eye to be examined effectively and naturally.

It is another object of the present invention to provide an eye refractive power measuring apparatus in which a fixation target system can be operated at the most proper speed correspondingly to the refractive power of an eye to be examined having a great individual difference, whereby wasted time can be eliminated.

DESCRIPTION OF THE PREFERRED EMBODIMENT

Figure 1:
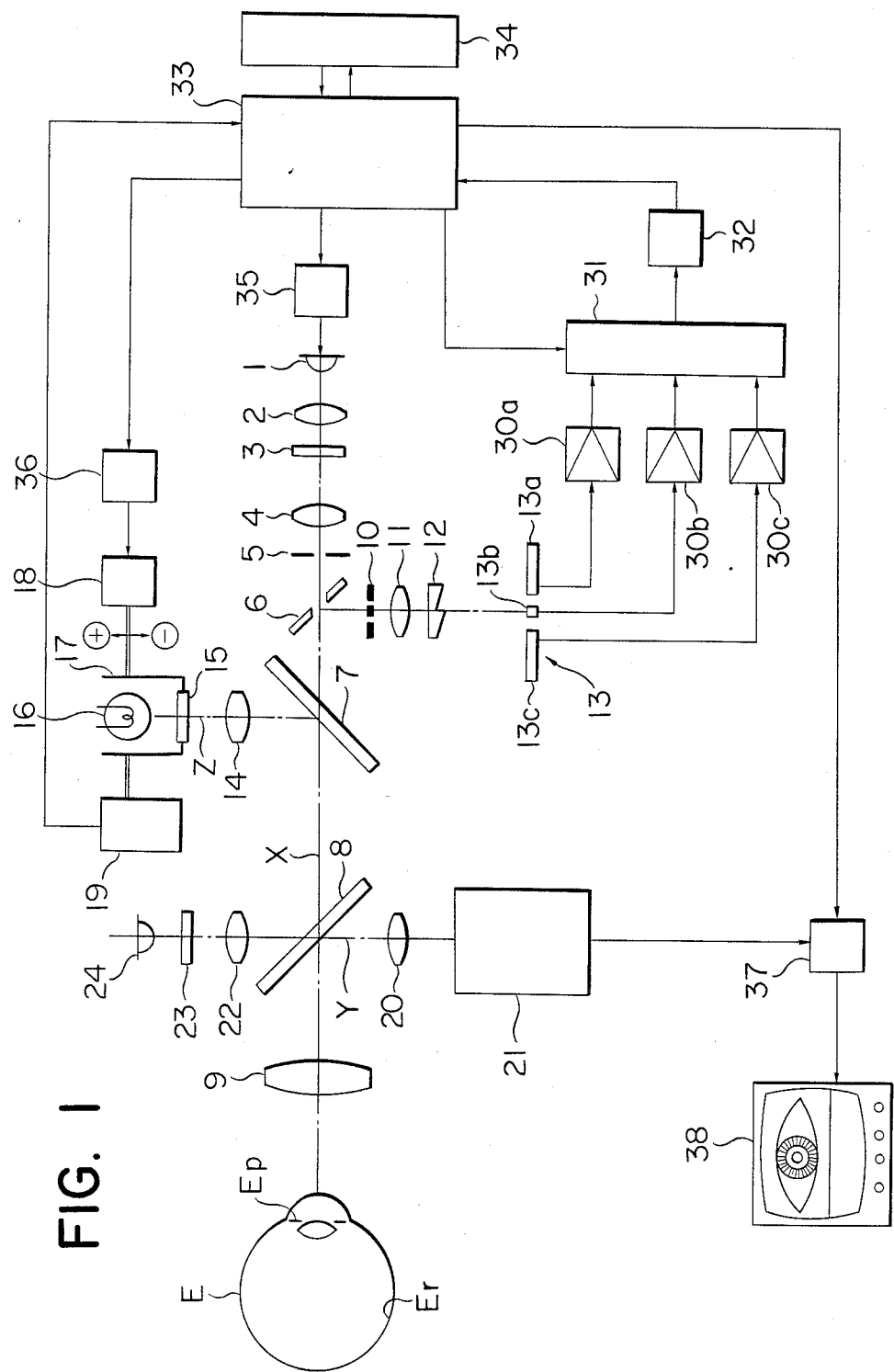
FIG. 1 shows the construction of an embodiment of the present invention.
Figure 2A:
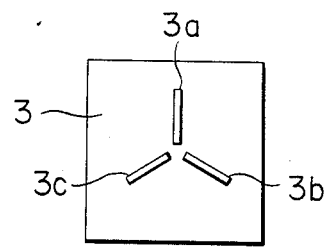
FIGS. 2A and 2B are front views of projection charts.
Figure 2B:
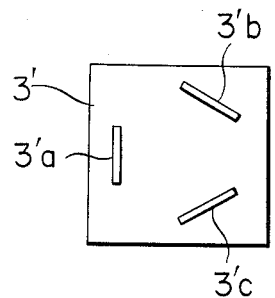

In FIG. 1, reference numeral 1 designates a light source emitting infrared rays. Between this light source 1 and an eye E to be examined and along the optic axis X of the light source 1, there are arranged in succession from the light source 1, a condensing lens 2, a projection chart 3, a relay lens 4, a stop 5, an apertured mirror 6, beam splitters 7, 8, and an objective lens 9. The projection chart 3, as shown, for example, in FIG. 2A or 2B, has three radially arranged slits $3a$, $3b$, $3c$ or $3'a$, $3'b$, $3'c$ forming an angle of 120° therebetween, the apertured mirror 6 is disposed in such a direction as to reflect a part of the reflected light from the eye E to be examined sideways, the beam splitter 7 is disposed in such a direction as to reflect the incident light from sideways thereof toward the eye E to be examined, and the beam splitter 8 is disposed in such a direction as to reflect a part of the reflected light from the eye E to be examined sideways and transmit therethrough the light beam incident from sideways thereof.

Figure 3:
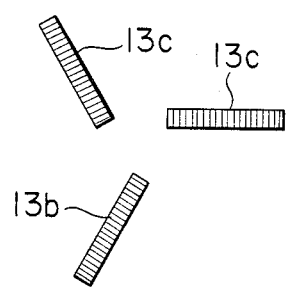
FIG. 3 is a front view showing an example of the arrangement of photodiode arrays.

On the reflection side of the apertured mirror 6 and along the optic axis thereof, there are arranged a stop 10, a relay lens 11, a prism 12 and a photodiode 13. The stop 10 has a ring-like light-transmitting portion having the central portion thereof shielded and divided into six parts, and the photodiode 13 is comprised of three radially arranged photodiode arrays $13a$, $13b$ and $13c$ as shown in FIG. 3. The prism 12 has a prism element corresponding to each meridian direction.

The infrared light emitted from the light source 1 is imaged at the center of the stop 5 by the condensing lens 2 and is further imaged on the pupil Ep of the eye E to be examined by the objective lens 9. Also, the image of the projection chart 3 disposed at that side of the condensing lens 2 which is adjacent to the relay lens is formed on the focal plane of the objective lens 9 by the relay lens 4 and is projected onto the fundus Er of the eye E by the objective lens 9. The aforementioned light beam emitted from the light source 1 passes through the central small aperture of the apertured mirror 6 and arrives at the fundus Er of the eye E, and the light beam reflected from the fundus Er of the eye E conversely passes through the objective lens 9, and then is reflected toward the stop 10 by the mirror portion of the apertured mirror 6. This light beam passes through six light-transmitting portions provided at equal intervals on the circumference of the stop 10, is subjected to the imaging action of the relay lens 11 and the deflecting action of the prism 12 and is imaged as two slit images for each measuring meridian on the photodiode arrays $13a$, $13b$, and $13c$ which are position detecting means. The angle of the light beam entering the prism 12 varies in accordance with the visibility of the eye to be examined and as a result, the spacing between the two images on each of the photodiode arrays $13a$–$13c$ varies. By photoelectrically detecting this spacing, automatic measurement of the visibility is accomplished. The basis of a measuring optical system having no such movable portion is known from Japanese Laid-open Patent Application No. 161031/1981.

Now, the beam splitter 7 has the characteristic of transmitting infrared light therethrough and refelecting visible light, and at the lateral incidence side of this beam splitter 7, there are disposed a relay lens 14, a fixation target 15 to be presented to the eye E to be examined, and a visible light source 16 for illuminating the fixation target. Also, a barrel 17 supporting the fixation target 15 and the light source 16 and provided with a cam mechanism movable in the direction of the optic axis Z, an electric motor 18 for moving the barrel 17 and a position detector 19 for detecting the position of the barrel 17 are provided as a fixation target system.

The beam splitter 8 has the characteristic of transmitting infrared light and visible light therethrough and reflecting only some wavelengths of the infrared light range, and at the lateral reflection side thereof, there are disposed an imaging lens 20 and a television camera 21. Also, at the opposite side of the beam splitter 8 on the optic axis Y of the imaging lens 20, there are provided in succession from the beam splitter 8 a projection lens 22, a target 23 for alignment and a light source 24.

Reference numerals 30 and so on designate an electrical system. The outputs from the aforementioned photodiode arrays 13a, 13b and 13c are amplified by amplifiers 30a, 30b and 30c, respectively, whereafter they are successively sent to an A/D converter 32 by a multiplexer 31, and the outputs A/D-converted by the A/D converter 32 are input to a microprocessor 33. The microprocessor 33 is connected to a memory 34, a driving circuit 35 for the infrared light source 1, driving circuit 36 for the electric motor 18, and a control circuit 37. The control circuit 37 produces a character signal in response to the video signal from the television camera 21 and the command from the microprocessor 33 and mixes it with the television image signal and puts out the same to a television monitor 38. The television monitor 38 is adapted to display the image of the front eye portion of the eye E to be examined, the target image projected by the infrared light source 24 and the target 23, and the final refraction value of the eye to be examined which has been measured and operated.

As previously described, in the present embodiment, the image of the projection chart 3 illuminated by the light source 1 is reflected by the fundus Er of the eye to be examined and is projected onto the photodiode arrays 13a, 13b and 13c through the objective lens 9, the beam splitters 8, 7, the apertured mirror 6, the stop 10, the relay lens 11 and the prism 12, but the reflected light beam from the fundus Er of the eye is separated by the stop 10 into three meridian directions to be measured, is deflected by the prism 12 and is imaged as two slit images corresponding to the meridian direction on each of the photodiode arrays 13a, 13b and 13c. These two slit images have the spacing therebetween varied in accordance with the visibility of the eye E to be examined because if the visibility of the eye E to be examined varies, the imaged position varies. Accordingly, the visibility can be measured by photoelectrically detecting the spacing between the slit images.

Operation of the entire apparatus will now be described. The examiner effects alignment by bringing the pupil Ep of the eye to be examined and the image of the target 23 into coincidence with each other while seeing the screen of the television monitor 38, whereafter the examiner imparts a measurement command signal to the microprocessor 33. On the other hand, the eye E to be examined is observing the fixation target 15 illuminated by the visible light source 16, through the relay lens 14, the beam splitters 7, 8 and the objective lens 9. The fixation target 15 lies at a predetermined position, and signals corresponding to the degree of refraction in the state in which the eye E to be examined is seeing the fixation target 15 are put out from the photodiode arrays 13a, 13b and 13c, and these outputs are converted into digital values by the A/D converter 32 and are operated by the microprocessor 33, whereby the degree of sphericalness or the degree of equivalent sphericalness is calculated.

In the present embodiment, there is no mechanical movable portion but the time for processing the electrical signal is only required in the process wherein the degree of sphericalness is calculated after the measurement command signal is imparted, and therefore only a very short time is required. By the signal from the position detector 19 for detecting the position of the fixation target 15, the microprocessor 33 compares the degree of sphericalness of the eye E to be examined with the diopter value corresponding to the position of the fixation target 15 and moves the fixation target 15 so as to eliminate the adjusting power of the eye E to be examined.

Specifically, short-sightedness or long-sightedness is judged from the result of the first measurement, and during the second measurement, in the case of short-sightedness, the fixation target is once displaced toward the minus side (downwardly as viewed in FIG. 1), while in the case of long-sightedness, the fixation target is once displaced toward the plus side (upwardly as viewed in FIG. 1).

In this manner, the direction of movement of the fixation target is controlled during the second measurement, but it is to be understood that during the subsequent measurement, the fixation target image is moved slightly to this side of the fundus Er of the eye E to be examined, namely, only toward the plus side. The movement speed, i.e., the movement amount/movement time, in this case is calculated in accordance with the pre-incorporated program in the memory 34, and the microprocessor 33 imparts a command to the driving circuit 36 for the electric motor 18. This driving circuit 36 produces a pulse of a frequency according to the command for a predetermined time to thereby revolve the electric motor 18 and move the barrel 17 in the direction of the optic axis Z.

The driving electric motor 18 used herein is a pulse motor which can control the angle of rotation by the number of driving pulses, can control the speed of revolution by the frequency of the pulse, and can control the direction of revolution by changing over the phase of the pulse. Also, the means for converting the revolution of the electric motor 18 into the direction of the optic axis is a cylindrical cam often used in a zoom lens or the like, and in the present embodiment, such a cam curve that the variation in the diopter value of the fixation target 15 per unit angle of rotation of the cylindrical cam is constant is adopted. More specifically, if for example, a pulse of the positive phase is applied to the electric motor 18, the fixation target 15 will be moved by 0.25 D, and if four pulses of 4 Hz are applied to the electric motor 18, the fixation target 15 will be moved by 1 D per second. When the fixation target 15 is moved by the operated amount of movement in this manner, the microprocessor 33 again introduces the outputs of the photodiode arrays 13a, 13b and 13c thereinto and calculates the degree of sphericalness of the eye to be examined.

The fixation target 15 at this time is set somewhat more toward the plus than the degree of sphericalness of the eye E to be examined and therefore, if the eye E to be examined continues to follow the movement of the fixation target 15, the degree of sphericalness will be varied. With this amount of variation and the diopter value corresponding to the position of the fixation target as the reference, the microprocessor 33 calculated the next position and movement speed of the fixation target 15 and instructs the driving circuit 36 for the electric motor 18 to move the fixation target 15, and again measures and operates the degree of sphericalness. In this process, the fixation follow-up property of the eye E to be examined with respect to the movement of the fixation target 15 is judged, and control is effected such that when the follow-up property is poor, a long time per unit amount of movement is taken and in the converse case, the fixation target is moved faster.

That is, in the first stage, the fixation target 15 is set, for example, at a position +1 D, and let it be assumed that the degree of sphericalness at this time is s(D). In the second stage, measurement is effected with the fixation target 15 being changed in position from S to S+1 in 0.6 second. If the degree of sphericalness of the eye E to be examined at this time is S+0.75 D, the follow-up property is judged to be as good as 75%, and if the degree of sphericalness is S+0.25 D, the follow-up property is judged to be as poor as 25%, and if there is no variation, the follow-up property is 0, and if the degree of sphericalness is S-0.5, the follow-up property is negative. In the third stage, when the follow-up property is good, the fixation target is further moved by +1 D in 0.4 second. When the follow-up property is poor, the fixation target 15 is further moved by +0.5 D in 0.6 second. When the follow-up property becomes 0 or negative, measurement is discontinued.

As another method, judgement equations like the following equations are pre-incorporated into the memory 34 and control is effected on the basis of the follow-up property. As an example, $$\Delta D = x + 0.25$$

$$\Delta T = 0.25/x$$

where $\Delta D$ is the diopter amount by which the fixation target 15 is moved, x is the follow-up rate (the ratio of the amount of variation in the degree of sphericalness of the eye E to be examined in the aforedescribed second stage to the amount of movement of the fixation target, represented by a decimal: 0.75 in the case of the follow-up property of 75%), and $\Delta T$ is the time for which the fixation target is moved.

The diopter value corresponding to the position of the fixation target 15 and the degree of sphericalness of the eye E to be examined may be introduced into and stored in the memory 34 and taken out during operation.

Now, when the movement speed is to be changed, both $\Delta D$ and $\Delta T$ may be changed and in addition, $\Delta D$ is not changed but only $\Delta T$ may be changed, or $\Delta T$ is not changed but only $\Delta D$ may be changed.

Instead of moving the fixation target 15, the relay lens 14 may be moved.

In the movement of the fixation target 15 and the measurement and operation are repeated several times while the fixation follow-up property of the eye E to be examined is judged in this manner, the position of the fixation target 15 will be much more toward the plus than the degree of sphericalness for which the adjusting power of the eye E to be examined is loosened. That is, the eye E to be examined will only see a blurred image and the found degree of sphericalness of the eye to be examined will no longer vary or will conversely adjust itself and exhibit a negative follow-up property. Thus, if measurement is terminated at this point and the degree of sphericalness most toward the plus is selected in these processes, there will be obtained the degree of sphericalness of the far point of the eye E to be examined.

It is apparent that the present invention is also applicable to the other eye refractive power measuring apparatus than the above-described embodiment.

What we claim is:

1. An eye refractive power measuring apparatus having:
   means for projecting a predetermined index image onto the fundus of an eye to be examined;
   detecting means for detecting a light beam of said index image reflected from the eye fundus, with respect to a measuring meridian direction;
   means for calculating a refractive power of the eye on the basis of an output of said detecting means;
   means for moving an image of fixation target for fixing the eye to be examined among plural different positions in the direction of the optic axis; and
   means for controlling a moving speed of said fixation target image at each position on the basis of a comparison of a variation between positions in said calculated refractive power of the eye with a variation between positions in diopter value with respect to the position of the fixation target image.

2. An apparatus according to claim 1, wherein said moving speed is changed such that, when a follow-up property of the eye with respect to the variation of the eye refractive power during changing the position of the fixation target image is good, the fixation target is moved fast, and when the follow-up property is poor, the fixation target image is moved slowly.

3. The apparatus of claim 1, wherein said detecting means detects the spacing between the imaged positions of separated light beams.

4. An eye refractive power measuring apparatus having:
   means for projecting a predetermined index image onto a fundus of an eye to be examined;
   detecting means for detecting a light beam of said index image reflected from the eye fundus, with respect to a measuring meridian direction;
   means for calculating a refractive power of the eye on the basis of an output of said detecting means;
   means for moving an image of a fixation target for fixing the eye to be examined among plural different positions, in the direction of an optic axis; and;
   means for controlling a moving speed of said fixation target image at each position by changing at least a moving range of said fixation target image on the basis of a comparison of a variation between positions in said calculated refractive power of the eye with a variation between positions in diopter value with respect to the position of the fixation target image.

* * * * *

UNITED STATES PATENT AND TRADEMARK OFFICE
CERTIFICATE OF CORRECTION

PATENT NO. : 4,755,041
DATED : July 5, 1988
INVENTOR(S) : Yasuyuki Ishikawa, et al.

It is certified that error appears in the above-identified patent and that said Letters Patent is hereby corrected as shown below:

IN THE ABSTRACT

Line 6, change "operating" to --calculating--.

Line 13, change "operated" to --calculated--.

COLUMN 1

Line 20, change "near-sightedness" to --nearsightedness--.

Line 34, change "short" to --near- --.

Line 37, change "short-signtedness" to --nearsightedness--

Line 52, change "Conversery," to --Conversely,--.

COLUMN 3

Line 43, change "operated." to --calculated.--.

COLUMN 4

Line 26, change "short-sightedness or long-sightedness" to --nearsightedness or farsightedness--.

Line 28, change "short-" to --near- --.

Line 31, change "long-sightedness" to --farsightedness--.

UNITED STATES PATENT AND TRADEMARK OFFICE
CERTIFICATE OF CORRECTION

PATENT NO. : 4,755,041
DATED : July 5, 1988
INVENTOR(S) : Yasuyuki Ishikawa, et al.

It is certified that error appears in the above-identified patent and that said Letters Patent is hereby corrected as shown below:

COLUMN 5

Line 4, after "plus" insert --side--.

Line 10, change "calculated" to --calculates--.

Line 66, change "and" to --,--.

COLUMN 6

Line 28, before "fixation" insert --a--.

Line 58, after "and" delete the semicolon.

IN THE DRAWINGS:

Sheet 2, Fig. 3, change the upper-left reference numeral "13c" to --13a--.

Signed and Sealed this

Ninth Day of May, 1989

*Attest:*

DONALD J. QUIGG

*Attesting Officer*     *Commissioner of Patents and Trademarks*